United States Patent [19]

Baker et al.

[11] 4,070,486
[45] Jan. 24, 1978

[54] N-SUBSTITUTED-N-(1-SUBSTITUTED-1-METHYL-2-PROPYNYL)-α-(SUBSTITUTED PHENOXY) ALKYLAMIDES AND THEIR USE AS MITICIDES

[75] Inventors: Don R. Baker, Orinda; Francis H. Walker, Mill Valley, both of Calif.

[73] Assignee: Stauffer Chemical Company, Westport, Conn.

[21] Appl. No.: 717,835

[22] Filed: Aug. 25, 1976

Related U.S. Application Data

[63] Continuation of Ser. No. 591,730, June 30, 1975, abandoned.

[51] Int. Cl.² .......................... A01N 9/20; A01N 9/24
[52] U.S. Cl. ................................... 424/324; 260/559 B
[58] Field of Search ...................... 424/324; 260/559 B

[56] References Cited

U.S. PATENT DOCUMENTS 3,272,844 9/1966 Easton et al. .................... 260/559 B Primary Examiner—V. D. Turner
Attorney, Agent, or Firm—M. Henry Heines; Michael J. Bradley

[57] ABSTRACT

Miticidally active compounds, defined by the generic formula

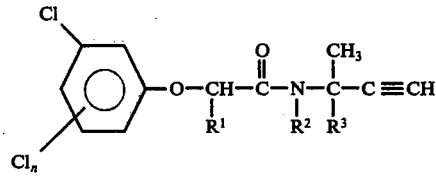

wherein $R^1$ is either methyl or ethyl; $R^2$ and $R^3$ are independently either hydrogen or methyl, and $n$ is 1 or 2, are described herein.

19 Claims, No Drawings

N-SUBSTITUTED-N-(1-SUBSTITUTED-1-METHYL-2-PROPYNYL)-α-(SUBSTITUTED PHENOXY) ALKYLAMIDES AND THEIR USE AS MITICIDES

This is a continuation, of application Ser. No. 591,730, filed June 30, 1975, now abandoned.

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat. No. 2,426,885 and its two continuations-in-part, U.S. Pat. No. 2,484,295 and U.S. Pat. No. 2,484,296. Herbicidal properties of such compounds are taught in U.S. Pat. Nos. 3,272,844, 3,439,018 and 3,564,607, and Belgian Pat. No. 739,714.

BRIEF DESCRIPTION OF THE INVENTION

This invention relates to a class of substituted acetylenic amides and to their use as miticides when used in a miticidally effective amount. More specifically, this invention relates to N-substituted-N-(1-substituted-1-methyl-2-propynyl)-α-(substituted phenoxy) alkylamides having the formula

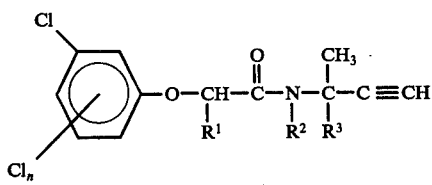

wherein $R^1$ is either methyl or ethyl; $R^2$ and $R^3$ are independently either hydrogen or methyl; and when $R^3$ is hydrogen, $n$ is either 1 or 2; and when $R^3$ is methyl, $n$ is 2. The chlorine atoms whose positions on the phenyl ring are undesignated in the above formula will hereinafter be referred to as "floating chlorine atoms." In the examples cited hereinbelow and in the claims which follow this specification, the floating chlorine atoms will be assigned positions on the phenyl ring. These positions will be identified in accordance with the following numbering system:

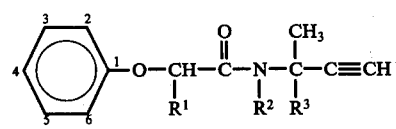

By miticidally effective amount is meant the amount of the herein disclosed miticidal compounds which when applied to the habitat of mites in any conventional manner will kill or substantially injure a significant portion of the population thereon.

DETAILED DESCRIPTION OF THE INVENTION

The compounds of the present invention are prepared by the following general method, wherein $R^1$, $R^2$, $R^3$ and $n$ are as defined above:

Reaction No. 1

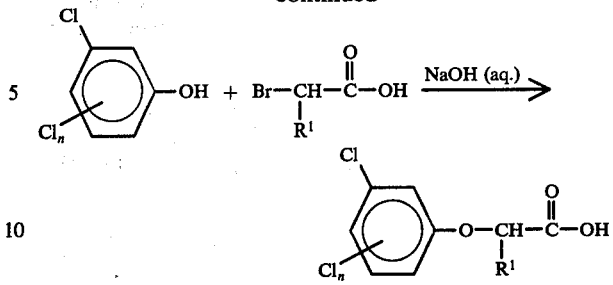

To a mixture of a molar amount of the phenol and a slight molar excess of the acid is added a slight molar excess of 50% aqueous NaOH. The product acid is then washed with suitable solvents and recovered from the organic phase.

Reaction No. 2

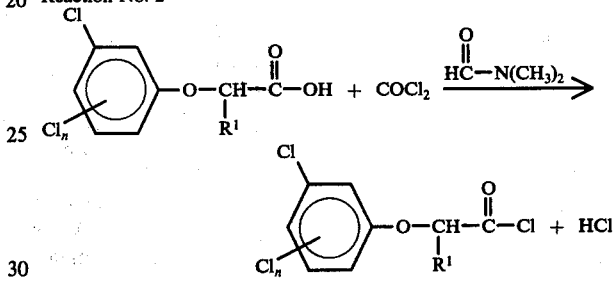

A slight molar excess of phosgene is introduced into a molar amount of the acid in a suitable solvent, to which a small amount of dimethyl formamide has been added. The excess phosgene and HCl are then removed and the solvent is evaporated to leave the acid chloride.

Reaction No. 3

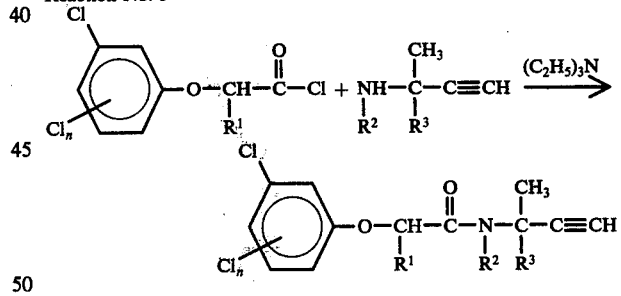

The acid chloride is added to a solution containing both the acetylenic amine and the triethylamine at 10°-15° C. After successive washings, the product is recovered from the organic phase.

The examples shown herein are illustrative of the method of preparation of the compounds of the invention.

EXAMPLE I

N-dimetlylpropynyl-α-(2,3,5-trichlorophenoxy)butyramide.

(Compound No. 3 in Table I below)

44.0 g (0.55 mole) of 50% aqueous sodium hydroxide was added to a mixture of 42.5 g (0.22 mole) 2,3,5-trichlorophenol and 43.4 g (0.26 mole) 2-bromobutyric acid, with rapid stirring at an initial temperature of 15° C. The temperature rose to 45° C over the course of the addition and was held between 15° C and 45° C with a cold water bath. At the completion of the sodium hydroxide addition, the cold bath was removed and the mixture was heated to 110° C for 15 minutes. Then 50 ml water, 53 ml perchloroethylene, and 42 ml concentrated hydrochloric acid were added to the reaction mixture and the mixture was heated to 85° C, then phase-separated. The organic layer was cooled and the product, α-(2,3,5-trichlorophenoxy)butyric acid crystallized. The acid was separated by filtration to give 43.1 g (69.1% yield) of the acid, m.p. 65°–70° C.

0.2 ml dimethyl formamide was added to a slurry of 50.3 g (0.18 mole) of α-(2,3,5-trichlorophenoxy)butyric acid in 80 ml toluene. The slurry was then heated to 60° C in a 500 ml flask which was fitted with a gas-inlet tube, a stirrer, a thermometer, and a dry ice-isopropyl alcohol condenser. 22 g (0.23 mole) of phosgene was passed into the mixture at a moderate rate. The dry ice condenser was then removed and replaced with a water-cooled condenser. Excess phosgene and HCl were removed by an argon purge through the solution at 60° C. The solution was then cooled and the solvent was removed in vacuum to leave 43.4 g (80% yield) of an oil, α-(2,3,5-trichlorophenoxy)butyryl chloride.

8.0 g (0.03 mole) of the acid chloride was added dropwise to a mixture of 2.9 g (0.035 mole) dimethylpropargylamine and 3.6 g (0.035 mole) triethylamine in 100 ml of dichloromethane at 10°–15° C. Some cooling in an ice bath was necessary to maintain the temperature. After the addition of the acid chloride, the mixture was allowed to come to room temperature and the product was isolated by washing with, in succession, 100 ml portions of water, dilute HCl, 5% Na₂CO₃ solution, and water. The organic phase was dried over magnesium sulfate and the solvent was removed in vacuum to leave 7.7 g (73.6% yield) of an oil, m.p. 118°–120° C, which was identified by infrared spectroscopy as N-dimethylpropynyl-α-(2,3,5-trichlorophenoxy)butyramide.

EXAMPLE II

N-methyl-N-isobutynyl-α-(2,3,5-trichlorophenoxy)-butyramide.

(Compound No. 4 in Table I below)

α-(2,3,5-trichlorophenoxy)butyryl chloride was prepared in a manner identical to that described in Example I. 7.0 g (0.02 mole) of the acid chloride was added dropwise to a mixture of 2.3 g (0.03 mole) of N-methyl-2-amino-3-butyne and 2.9 g (0.03 mole) of triethylamine in 100 ml dichloromethane at 10°–15° C. From this point a procedure identical to that of Example I was followed, to yield 7.1 g (84.8% yield) of N-methyl-N-isobutynyl-α-(2,3,5-trichlorophenoxy)butyramide, m.p. 73°–77° C, characterized by infrared spectroscopy.

Other compounds, such as those included in the following table, can be prepared in a manner analogous to that shown in the examples above, starting with the appropriate materials. The compounds in the table are representative of those embodied in the present invention. Compound numbers have been assigned to them for purposes of identification throughout the balance of the specification.

TABLE I

| COMPOUND NUMBER | COMPOUND | m.p. ° C. or $n_D^{20}$ |
|---|---|---|
| 1 | Cl-C₆H₂(Cl)(Cl)-O-CH(C₂H₅)-C(=O)-N(CH₃)-CH(CH₃)-C≡CH | 1.5374 |
| 2 | Cl-C₆H₂(Cl)(Cl)-O-CH(C₂H₅)-C(=O)-NH-C(CH₃)₂-C≡CH | 78–83° C |
| 3 | (2,3,5-Cl₃)C₆H₂-O-CH(C₂H₅)-C(=O)-NH-C(CH₃)₂-C≡CH | 118–120° C |
| 4 | (2,3,5-Cl₃)C₆H₂-O-CH(C₂H₅)-C(=O)-N(CH₃)-CH(CH₃)-C≡CH | 73–77° C |
| 5 | Cl-C₆H₂(Cl)(Cl)-O-CH(C₂H₅)-C(=O)-N(CH₃)-CH(CH₃)-C≡CH | 88–98° C |

TABLE I-continued

| COMPOUND NUMBER | COMPOUND | m.p. °C. or $n_D^{30}$ |
|---|---|---|
| 6 | 2,3,4-trichlorophenyl-O-CH(CH₃)-C(=O)-NH-C(CH₃)₂-C≡CH | 121–123° C |
| 7 | 2,3,5-trichlorophenyl-O-CH(CH₃)-C(=O)-N(CH₃)-CH(CH₃)-C≡CH | 1.5486 |

Miticidal activity of each of the above compounds on the two-spotted mite [*Tetranychus urticae* (Koch)] was evaluated as follows:

Pinto bean plants (Phaseolus sp.), approximately 10 cm tall, are transplanted into sandy loam soil in 3-inch clay pots and thoroughly infested with two-spotted mites of mixed ages and sexes. Twenty-four hours later the infested plants are inverted and dipped for 2–3 seconds in 50—50 acetone-water solutions of the test chemicals. Treated plants are held in the greenhouse, and seven days later mortality is determined for both the adult mites and the nymphs hatching from eggs which were on the plants at the time of treatment. Test concentrations range from about 0.08% down to that at which 50% mortality occurs.

The following is a table of the results of the above test procedure, indicating the effective concentration at which 50% mortality was achieved.

TABLE II

Effective Concentrations on Two-Spotted Mite
[*Tetranychus urticae* (Koch)]

| COMPOUND NUMBER | PE (%) | Eggs (%) |
|---|---|---|
| 1 | .03 | >.05 |
| 2 | .03 | >.05 |
| 3 | .001 | .008 |
| 4 | .005 | .03 |
| 5 | .08 | .05 |
| 6 | .005 | .008 |
| 7 | .05 | >.05 |

PE = Post-embryonic
\> = Greater than

Neither the examples nor the tables hereinabove are intended to limit the invention in any manner.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in mitcide preparations. One such composition can contain either a single miticidally active compound or a combination of miticidally active compounds. The miticide compositions of this invention can contain as adjuvants organic solvents such as sesame oil, xylene, or heavy petroleum; water; emulsifying agents; surface active agents; talc; pyrophyllite; diatomite; gypsum; clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence such as light, or by some physiological action which the compound induces when it is ingested into the body of the pest.

The precise manner in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

We claim:

1. A method of controlling mites comprising applying to said mites a miticidally effective amount of a compound having the formula

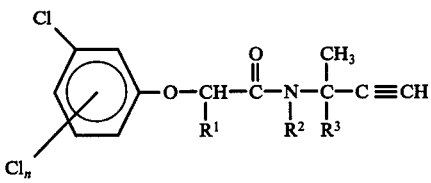

wherein $R^1$ is either methyl or ethyl; $R^2$ and $R^3$ are independently either hydrogen or methyl; and when $R^3$ is hydrogen, $n$ is either 1 or 2; and when $R^3$ is methyl, $n$ is 2.

2. A method according to claim 1 in which $R^1$ is ethyl.

3. A method according to claim 1 in which $R^3$ is methyl.

4. A method according to claim 1 in which $R^1$ is ethyl, $R^2$ is hydrogen, and $R^3$ is methyl.

5. A method according to claim 4 in which the two floating chlorine atoms occupy the 2- and 4-positions on the phenyl ring.

6. A method according to claim 4 in which the two floating chlorine atoms occupy the 2- and 5-positions on the phenyl ring.

7. A method according to claim 1 in which $R^3$ is hydrogen.

8. A method according to claim 1 in which $R^1$ is ethyl, $R^2$ is methyl, and $R^3$ is hydrogen.

9. A method according to claim 8 in which $n$ is 1.

10. A method according to claim 9 in which the floating chlorine atom occupies the 4-position on the phenyl ring.

11. A method according to claim 8 in which $n$ is 2.

12. A method according to claim 11 in which the two floating chlorine atoms occupy the 2- and 4-positions on the phenyl ring.

13. A method according to claim 11 in which the two floating chlorine atoms occupy the 2- and 5-positions on the phenyl ring.

14. A method according to claim 1 in which $R^1$ is methyl.

15. A method according to claim 1 in which $R^1$ is methyl, $R^2$ is hydrogen, and $R^3$ is methyl.

16. A method according to claim 15 in which the two floating chlorine atoms occupy the 2- and 5-positions on the phenyl ring.

17. A method according to claim 1 in which $R^1$ is methyl, $R^2$ is methyl, and $R^3$ is hydrogen.

18. A method according to claim 17 in which $n$ is 2.

19. A method according to claim 18 in which the two floating chlorine atoms occupy the 2- and 5-positions on the phenyl ring.

* * * * *